United States Patent
Vincent et al.

(10) Patent No.: US 7,731,414 B2
(45) Date of Patent: Jun. 8, 2010

(54) REAGENT CARTRIDGE MIXING TUBE

(75) Inventors: Kathleen Vincent, Pelham, NH (US); Mark Talmer, Pepperell, MA (US); Gerhardt P. Schroeder, Londonderry, NH (US)

(73) Assignee: Instrumentation Laboratory Company, Bedford, MA (US)

( * ) Notice: Subject to any disclaimer, the term of this patent is extended or adjusted under 35 U.S.C. 154(b) by 360 days.

(21) Appl. No.: 11/704,001

(22) Filed: Feb. 8, 2007

(65) Prior Publication Data

US 2008/0192567 A1    Aug. 14, 2008

(51) Int. Cl.
*B01F 11/00* (2006.01)
(52) U.S. Cl. .................. 366/211; 210/222; 366/228; 366/237; 436/526
(58) Field of Classification Search ............ 34/588, 34/602; 68/9, 10, 11, 27, 133, 174; 215/DIG. 3, 215/DIG. 8; 366/14, 198, 202, 210, 211, 366/228, 229, 237; 422/913, 914, 918; D9/520, D9/556, 569; D24/216, 224; 210/222; 436/526
See application file for complete search history.

(56) References Cited

U.S. PATENT DOCUMENTS

| | | | | | |
|---|---|---|---|---|---|
| 8,279 | A | * | 8/1851 | Chase | 235/52 |
| 33,146 | A | * | 8/1861 | Harsha | 68/174 |
| 67,801 | A | * | 8/1867 | Rawdon et al. | 68/173 |
| 106,220 | A | * | 8/1870 | Shepard | 68/173 |
| 400,637 | A | * | 4/1889 | Cole | 68/22 R |
| 499,937 | A | * | 6/1893 | Renson | 68/58 |
| 502,283 | A | * | 8/1893 | Crompton | 366/183.3 |
| 1,176,678 | A | * | 3/1916 | Heaphy | 366/135 |
| 1,358,405 | A | * | 11/1920 | Young et al. | 68/139 |
| 1,644,959 | A | * | 10/1927 | Snyder | 68/27 |
| 1,717,177 | A | * | 6/1929 | Altorfer | 68/133 |
| 1,759,390 | A | * | 5/1930 | Brandt | 211/74 |
| 1,806,982 | A | * | 5/1931 | McKercher | 68/53 |
| 1,897,239 | A | * | 2/1933 | Chapman | 68/133 |
| 1,898,221 | A | * | 2/1933 | Snyder | 68/174 |
| 1,930,241 | A | * | 10/1933 | Labisky | 68/79 |

(Continued)

FOREIGN PATENT DOCUMENTS

EP    0712000    9/1995

(Continued)

OTHER PUBLICATIONS

Siemens Global website @ http://diagnostics.siemens.com/webapp/wcs/stores/servlet/Product, for ACS:180® SE Automated Chemiluminescence System accessed Jun. 13, 2007, © Siemens AG, 2007.

(Continued)

*Primary Examiner*—David L Sorkin
*Assistant Examiner*—Andrew Janca
(74) *Attorney, Agent, or Firm*—Burns & Levinson LLP

(57) ABSTRACT

Embodiments of the invention relate to a clinical instrument analyzer system for the automated analysis of patient samples. In one embodiment, the analyzer may be used to analyze bodily fluid samples, such as blood, plasma, serum, urine or cerebrospinal fluid, for example. Embodiments of the invention relate to an apparatus and method for suspending magnetic particles accumulated on the floor of a mixing tube and depositing the magnetic particles in bodily fluid samples.

19 Claims, 12 Drawing Sheets

U.S. PATENT DOCUMENTS

| | | | | |
|---|---|---|---|---|
| 2,298,624 | A * | 10/1942 | Labisky | 68/4 |
| 2,867,107 | A * | 1/1959 | Brown | 68/24 |
| 3,008,317 | A * | 11/1961 | Beshur | 68/213 |
| 3,087,776 | A * | 4/1963 | Anderson | 8/159 |
| 3,325,031 | A * | 6/1967 | Singier | 215/247 |
| 3,341,184 | A * | 9/1967 | Merrill | 366/349 |
| D209,822 | S * | 1/1968 | Alliger | D24/224 |
| 3,397,867 | A * | 8/1968 | van't Hoff | 366/341 |
| 3,432,149 | A * | 3/1969 | Berglund et al. | 366/202 |
| 3,578,291 | A * | 5/1971 | Oberli | 366/211 |
| 3,606,262 | A * | 9/1971 | van't Hoff | 366/341 |
| D222,352 | S * | 10/1971 | Ferro | D24/224 |
| 3,760,972 | A * | 9/1973 | McKirnan | 220/592.16 |
| 3,970,518 | A * | 7/1976 | Giaever | 435/239 |
| 4,051,773 | A * | 10/1977 | Staton | 99/622 |
| 4,125,187 | A * | 11/1978 | Vecchiotti | 429/176 |
| 4,225,246 | A * | 9/1980 | Bridge | 366/40 |
| 4,259,289 | A | 3/1981 | Curry et al. | |
| 4,278,437 | A * | 7/1981 | Haggar | 436/165 |
| 4,521,116 | A * | 6/1985 | Adsit | 366/54 |
| 4,756,623 | A * | 7/1988 | Bishop | 366/57 |
| 4,785,953 | A * | 11/1988 | Buchholz et al. | 215/365 |
| 4,895,650 | A * | 1/1990 | Wang | 210/222 |
| 4,943,164 | A * | 7/1990 | Ohishi et al. | 366/149 |
| 5,118,198 | A * | 6/1992 | Whiteman, Jr. | 366/47 |
| 5,128,103 | A * | 7/1992 | Wang et al. | 422/64 |
| 5,403,086 | A * | 4/1995 | Lindesay | 366/59 |
| 5,492,401 | A * | 2/1996 | Halsted | 366/47 |
| 5,501,841 | A * | 3/1996 | Lee et al. | 422/101 |
| 5,540,890 | A | 7/1996 | Clark et al. | |
| 5,594,164 | A | 1/1997 | Bull | |
| 5,599,501 | A | 2/1997 | Carey et al. | |
| D383,851 | S * | 9/1997 | Wong | D24/224 |
| 5,683,658 | A * | 11/1997 | Reischl et al. | 422/102 |
| 5,774,772 | A * | 6/1998 | Kai et al. | 399/260 |
| 5,795,784 | A * | 8/1998 | Arnquist et al. | 436/50 |
| 5,856,194 | A * | 1/1999 | Arnquist et al. | 436/50 |
| 5,888,835 | A | 3/1999 | Bushnell et al. | |
| 5,934,800 | A * | 8/1999 | Bonacci | 366/47 |
| 5,985,671 | A | 11/1999 | Leistner et al. | |
| 6,048,496 | A | 4/2000 | Zhou et al. | |
| 6,149,872 | A | 11/2000 | Mack et al. | |
| 6,238,330 | B1 * | 5/2001 | Marziali | 494/31 |
| 6,413,420 | B1 | 7/2002 | Foy et al. | |
| 6,436,349 | B1 * | 8/2002 | Carey et al. | 422/64 |
| 6,444,174 | B1 * | 9/2002 | Lascombes | 422/102 |
| 6,562,239 | B2 | 5/2003 | Foy et al. | |
| 6,562,298 | B1 * | 5/2003 | Arnquist et al. | 422/63 |
| 6,672,458 | B2 * | 1/2004 | Hansen et al. | 209/224 |
| 6,910,801 | B2 * | 6/2005 | Sasaki | 366/220 |
| 7,011,794 | B2 * | 3/2006 | Kagan et al. | 422/102 |
| D565,741 | S * | 4/2008 | Vincent et al. | D24/216 |
| 2003/0044323 | A1 | 3/2003 | Diamond et al. | |
| 2004/0040346 | A1 * | 3/2004 | Hawkins et al. | 68/174 |
| 2006/0081539 | A1 * | 4/2006 | Safar et al. | 210/695 |
| 2008/0192567 | A1 * | 8/2008 | Vincent et al. | 366/198 |

FOREIGN PATENT DOCUMENTS

| | | |
|---|---|---|
| EP | 0806665 | 5/1997 |
| EP | 0889328 | 10/1997 |
| JP | 1028561 | 1/1989 |
| JP | 8146001 | 6/1996 |
| JP | 10123136 | 5/1998 |
| JP | 2000111557 | 4/2000 |
| JP | 2001116752 | 4/2001 |
| WO | WO98/18008 | 4/1998 |
| WO | WO 02/37078 | 5/2002 |
| WO | 03/020427 | 3/2003 |

OTHER PUBLICATIONS

International Search Report for International Application No. PCT/US2008/052948, dated Jul. 8, 2008 (2 pages).

* cited by examiner

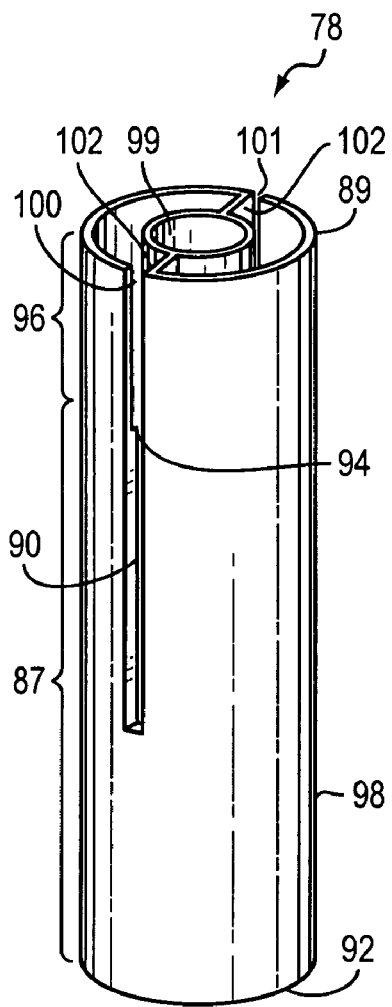
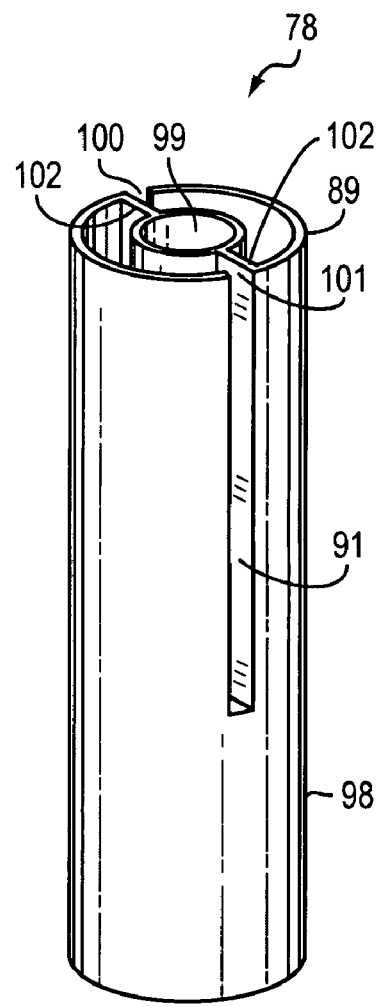
FIG. 3E  FIG. 3F
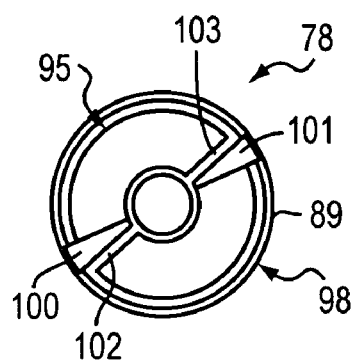
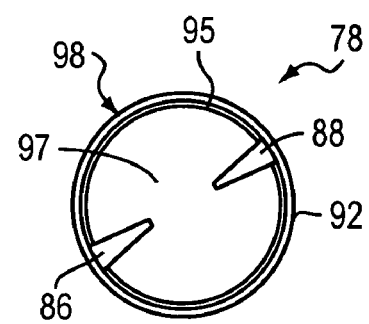
FIG. 5  FIG. 4

REAGENT CARTRIDGE MIXING TUBE

FIELD OF THE INVENTION

The present invention relates to a clinical instrument analyzer system and specifically to a reagent cartridge mixing tube.

BACKGROUND OF THE INVENTION

Separation, isolation, and concentration are process steps common to a chemical analysis. Often, these steps are taken to remove interfering substances so that a subsequent chemical analysis can be performed. This separation stage can be performed in several ways including solvent extraction, solvent evaporation, and resin exchange. Magnetic separation, another technique for removing interfering substances, is a process of separation, isolation, and concentration where the sought-for substance is attached or bound to magnetic particles. The magnetic particles offer advantages of handling including speed, convenience, and low energy input. They are particularly suited to handling small samples.

In order to administer a magnetic separation, a threshold number of magnetic particles needs to be present in the solution to be measured. However, magnetic particles are more dense than most of the other particles in the solutions in which they are mixed. Therefore, the magnetic particles will accumulate at the bottom of their holding receptacles. Previous reagent cartridges for holding magnetic particle solutions or suspensions have used continuous mixing to ensure that appropriate concentrations of magnetic particles are distributed throughout the magnetic solution. However, continuous mixing can be expensive, inefficient, and prone to mechanical failures. The present invention addresses these shortcomings of prior art magnetic particle mixing tubes.

SUMMARY OF THE INVENTION

In satisfaction of the above-mentioned needs and others, the present teachings relate to a system for suspending magnetic particles.

The system includes a reagent cartridge including a reagent holder for holding a plurality of tubes. The plurality of tubes may include a mixing tube for holding particles. The mixing tube may be rotatably mounted in the holder. The mixing tube may include a lower section, an interior surface, an exterior surface, a first agitating member, and a second agitating member. The first agitating member and the second agitating member extend from the interior surface into the lumen of the mixing tube. The dimensions and positioning of the first agitating member correspond to a first longitudinal groove on the exterior surface of the mixing tube. The dimensions and positioning of the second agitating member correspond to a second longitudinal groove on the exterior of the mixing tube. The mixing tube may further include at least one slot and a longitudinally positioned cylindrical member, positioned on the lower section of said mixing tube. The system may further include a motor operatively connectable to the slot and the cylindrical member. The motor may have a linear actuator for engaging the slot and the cylindrical member in the lower section of the mixing tube via a set of pins. The rotation of the linear actuator may actuate the agitating members thereby suspending the particles.

In one embodiment the particles are magnetizable.

In one embodiment, the first agitating member is opposite the second agitating member. In another embodiment, the mixing tube has three agitating members. The first agitating member and said second agitating member may be substantially triangular, semi-circular, or rectangular in cross-section. In another embodiment, the first agitating member and the second agitating member are blades.

In one embodiment, the linear actuator includes a third pin and the mixing tube includes a second slot for engaging the third pin of the linear actuator.

The mixing tube may be cylindrical, frustoconical, sealed, detachable from the holder, and/or extrusion molded.

In one embodiment, the system includes a plurality of reagent tubes. The reagent tubes may be detachable from the holder and/or may be substantially rectangular in cross-section or cylindrical.

Another aspect of the present teachings relates to a method of suspending particles in solution including dispensing particle solution into a mixing tube, wherein the mixing tube comprises a cylinder with a first agitating member and a second agitating member, engaging the mixing tube with a motor, rotating the mixing tube via the motor according to a mixing protocol, and disengaging the motor from the mixing tube.

The mixing protocol may include rotating the mixing tube in a first direction for a first period of time, and then rotating the mixing tube in a second direction for a second period of time. In another embodiment, the mixing protocol may include two phases: a first phase and a second phase. The first phase may include rotating the mixing tube one full rotation in both a first direction and a second direction. The second phase may include alternating the direction of rotation fifteen times.

Another aspect of the invention relates to method of manufacturing a mixing tube including molding a mixing tube for holding particles rotatably mounted in a holder. The mixing tube includes a top end and a lower section positioned on an end opposite to the top end, an interior surface, an exterior surface, a first agitating member, and a second agitating member. The first agitating member and the second agitating member extend from the interior surface into the lumen of the mixing tube. The dimensions and positioning of the first agitating member correspond to a first longitudinal groove on the exterior surface of the mixing tube. The dimensions and positioning of the second agitating member correspond to a second longitudinal groove on the exterior of said mixing tube. The mixing tube further includes at least one slot and a cylindrical member, longitudinally positioned on the lower section of the mixing tube. In one embodiment, the mixing tube is extrusion molded.

BRIEF DESCRIPTION OF THE DRAWINGS

These embodiments and other aspects of this invention will be readily apparent from the detailed description below and the appended drawings, which are meant to illustrate and not to limit the invention, and in which:

FIG. 3E is another side perspective view of the mixing tube according to an exemplary embodiment of the present invention.

FIG. 3F is another side perspective view of the mixing tube according to an exemplary embodiment of the present invention.

FIG. 4 is a top-view of a mixing tube according to an exemplary embodiment of the present invention.

FIG. 5 is a bottom-view of a mixing tube according to an exemplary embodiment of the present invention.

DESCRIPTION

The present invention will be more completely understood through the following description, which should be read in conjunction with the attached drawings. In this description, like numbers refer to similar elements within various embodiments of the present invention. Within this description, the claimed invention will be explained with respect to embodiments. The skilled artisan will readily appreciate that the methods and systems described herein are merely exemplary and that variations can be made without departing from the spirit and scope of the invention.

Embodiments of the invention relate to a clinical instrument analyzer system for the automated analysis of patient samples. In one embodiment, the analyzer may be used to analyze target biomolecules in bodily fluid samples, such as blood, plasma, serum, urine, or cerebrospinal fluid. The clinical instrument analyzer system according to the invention, for example, automates immunochemical assays for the detection of a target biomolecule in a patient sample. To detect the target biomolecule, a first antibody specific to the target biomolecule is labeled with a luminometric marker. A luminometric marker is a substance that is detectable in a luminometer. A second antibody specific to the target biomolecule is attached to a magnetic particle. The antibodies attached to the magnetic particles and the antibodies attached to the luminometric marker recognize the target biomolecules and bind to them in an immunochemical reaction. As a result, specific complexes composed of magnetic particles, luminometric markers, and target biomolecules are formed. These specific complexes then may be examined in a luminometer.

Embodiments of the invention also relate to an apparatus and method for uniformly suspending magnetic particles in solution in a mixing tube before aspirating an aliquot of the magnetic particle solution into a vial holding a patient sample. Subsequently, the presence and/or amount of target biomolecule will be determined in a diagnostic assay. The magnetic particles, due to their weight, tend to accumulate at the bottom of the mixing tube over time. As used herein, suspending the magnetic particles in the mixing tube refers to the removal of the particles from the mixing tube bottom and suspension of the magnetic particles in a solution in the mixing tube. Uniform dispersal of the magnetic particles in the solution is important to clinical analysis because any variability in the distribution of the magnetic particles in the solution will affect the accuracy of the diagnostic assay.

Figure 1A:
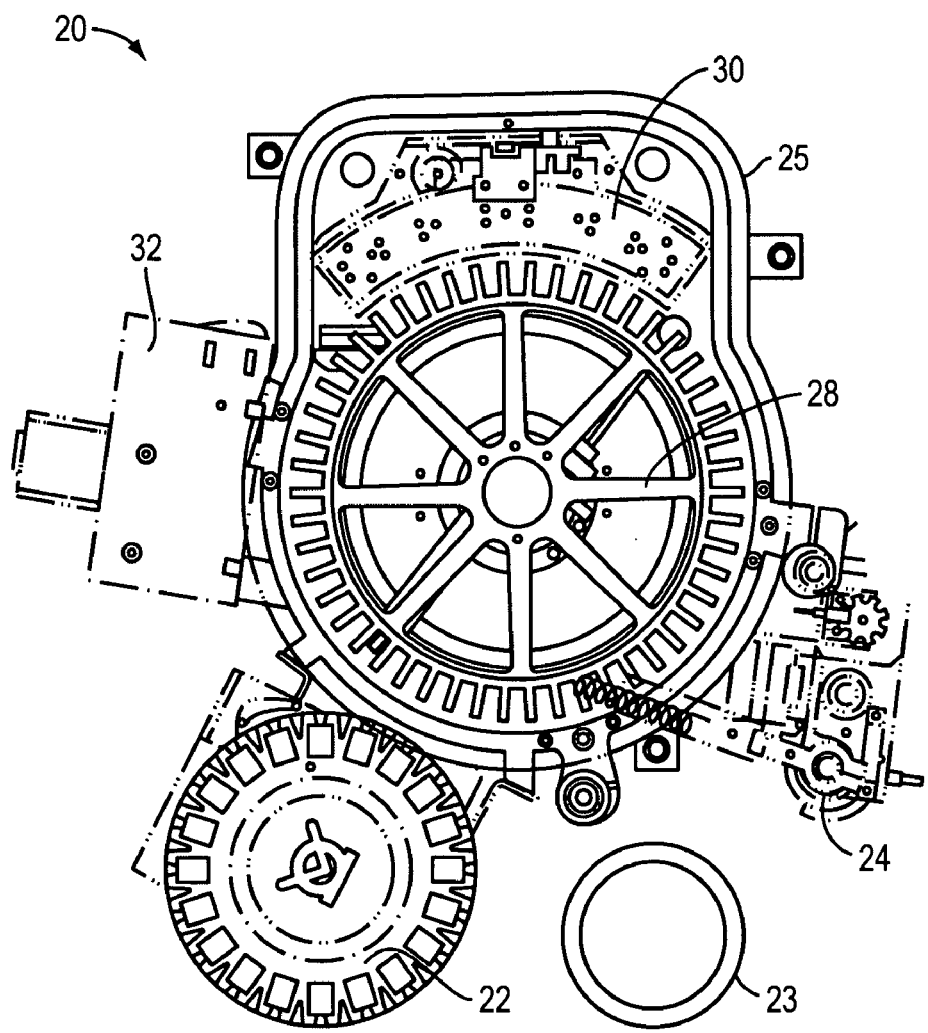
FIG. 1A is a top view of a clinical instrument analyzer system according to an exemplary embodiment of the present invention.

FIG. 1A is a top view of the clinical instrument analyzer system according to an embodiment of the present invention. The illustrated clinical instrument analyzer system 20 contains one or more stations or modules for treatment and analysis of patient samples contained in a vial (not shown in FIG. 1). The vial may be a cuvette, tube or any other receptacle suitable for holding a sample (not shown in FIG. 1). In one embodiment, the clinical instrument analyzer system 20 includes at least the following: a vial loader 22, a sample station (not shown) for adding a sample into a vial, a reagent station 23 for adding one or more reagents into the vial, a plurality of pipettes 24 for providing wash and rinse fluid to the vial, a carousel 28 for receiving one or more vials from the vial loader and distributing the vials, a magnetic washing module 30, a luminometer 32, and a heater module 25 to incubate the vial.

In one embodiment, the vial loader 22 holds a plurality of vials. The vial loader 22 may, for example, load vials onto the carousel 28 as described in the concurrently filed U.S. patent application entitled "Apparatus and Methods for Dispensing Sample Holders". In some embodiments, the vial loader 22 comprises a rotatable carousel with vertical slots to hold stacks of vials. The vials may be stacked in a sleeve, for example, and the sleeve may be inserted into the vial loader 22. The vial loader 22 expels a vial from the sleeve on to the carousel 28.

With continued reference to FIG. 1A, the carousel 28, in one embodiment, holds, and/or distributes a plurality of vials to various stations or modules such as, for example, the sample station, the reagent station 23, the magnetic washing module 30, the heater module, or the luminometer 32 in the clinical instrument analyzer system 20. The exemplary carousel 28 is operably joined to a motor and rotates, for example. A vial in the carousel 28 may be presented to any one of a plurality of stations or modules proximate to it. In one embodiment, a transfer arm (not shown) permits movement of vials from the carousel 28 to the various stations or modules of the clinical instrument analyzer system 20.

A sample adding station (not shown) in one embodiment, deposits the selected sample in the vial.

With continued reference to FIG. 1A, the magnetic washing module 30 is configured to permit washing of the magnetic particles present in the vial. The magnetic washing module 30 includes one or more magnet stations, containing magnetic arrays. A magnetic wash of the particles in the vial may be performed by securing the vial proximate to the magnetic array. The magnetic field of the magnet array in the magnet station penetrates the wall of the vial and attracts the magnetic particles present in the specific complexes toward the one or more magnetic arrays. Thus, the specific complexes clump together on the wall of the vial wall proximate to the magnet arrays, forming a pellet of specific complexes. While the particles are attracted to the magnetic arrays, the vial may be injected and/or aspirated with wash or rinse solution through the use of one or more pipettes to rinse and remove the non-complexed particles and the solution in the vial except for the specific complexes. The pellet of specific complexes is analyzed in the luminometer 32 for the magnitude of luminescence. The magnitude of luminescence is indicative of the concentration of the target molecule in the patient sample.

With continued reference to FIG. 1A, depending on the analysis to be conducted on the patient sample and which target biomolecule is to be analyzed, the reagent station 23 adds, for example, a rinse fluid, one or more antibodies against the target biomolecule, reagents for triggering a chemiluminescent reaction, buffers, other reagents, a luminometric marker substance containing luminogens, and/or magnetizable particles.

In some embodiments, the magnetizable particles are made of iron or any other magnetic or magnetizable material. In certain embodiments, the magnetic particles are paramagnetic, such that when the magnets are removed, the particles exhibit zero magnetization. The magnetic particles may be substantially uniform in diameter and may have a grain size, for example, in the range of 1-10 µm, 1.0 µm, 8.0 µm, or 4.7 µm, preferably. In one embodiment, for example, the exterior of the magnetizable particles are coated with a latex layer that contains the specific antibody against the target biomolecule. The magnetizable particles are held in a solution in a reagent mixing tube described in greater detail below. The solution may contain water, rinse fluids, or any other liquid necessary for the analysis.

Figure 1B:
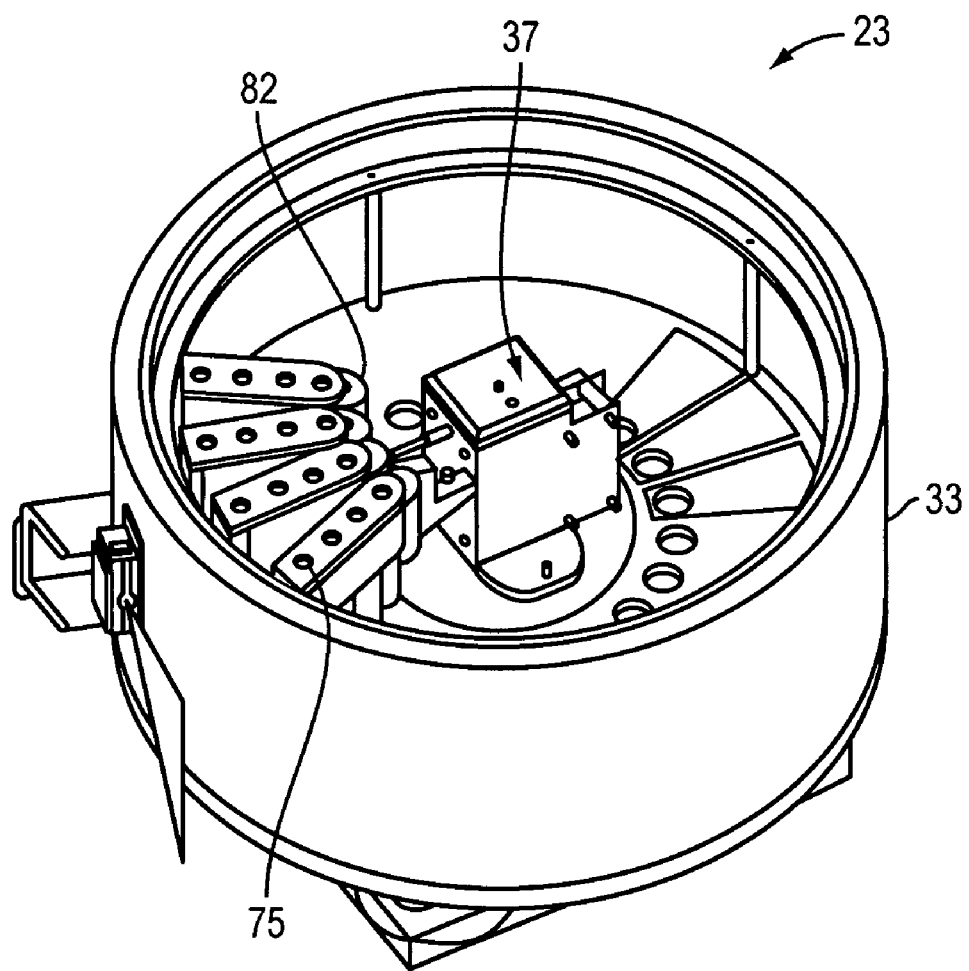
FIG. 1B is a perspective view of a reagent station according to an exemplary embodiment of the present invention.

FIG. 1B is a perspective view of the reagent station 23 according to an exemplary embodiment of the invention, the reagent station 23 includes a reagent station housing 33, a bar code scanner 37, and one or more reagent cartridges 75, wherein each reagent cartridge has a bar code 82. The reagent station housing 33 may be, for example, a bowl shaped container made of cast metal or plastic. One or more reagent cartridges 75 are stored within the reagent station bowl 33. For example, the reagent cartridges 75 may be radially distributed from the center of the bowl-shaped housing 33. In one embodiment, the reagent cartridges 75 are inserted in a rotation carousel (not shown) positioned in the reagent station housing 33. The reagent station housing 33 may be temperature and/or humidity controlled.

The reagent cartridge 75 contains one or more reagents which are injected into a vial. In one embodiment, the reagent cartridge 75 is wedge or pie shaped such that a plurality of reagent cartridges 75 may fit into the bowl-shaped reagent station housing 33. For example, five to thirty-five reagent cartridges 75, or more specifically, ten, twenty or thirty, or more reagent cartridges 75 may be placed into the reagent station housing 33 at one time, depending on the size of the reagent station housing 33.

With continued reference to FIG. 1B, the bar code scanner 37 permits a user to index and track the various reagent cartridges 75 in the reagent station housing 33. The bar code scanner 37 may read the bar code 82 placed on the side of the reagent cartridge 75 facing the bar code scanner 37. The bar code reading is transmitted to a computer processor that alerts the user of the clinical instrument analyzer system 20 (not shown) of the location of the various reagent cartridges 75 in the reagent station housing 33. Additionally, the bar code scanner 37 permits the user to electronically select various reagent cartridges 75 and the reagents contained therein for the desired target biomolecule analysis of the patient sample. The user may request specific reagents and the bar code scanner 37 identifies the corresponding reagent cartridge 75 containing those reagents. Thus, the bar code label 82 may be used to distinguish between different reagents in the reagent cartridges 75 and may assist a user to determine the location of certain reagents within the reagent station 23.

Figure 2A:
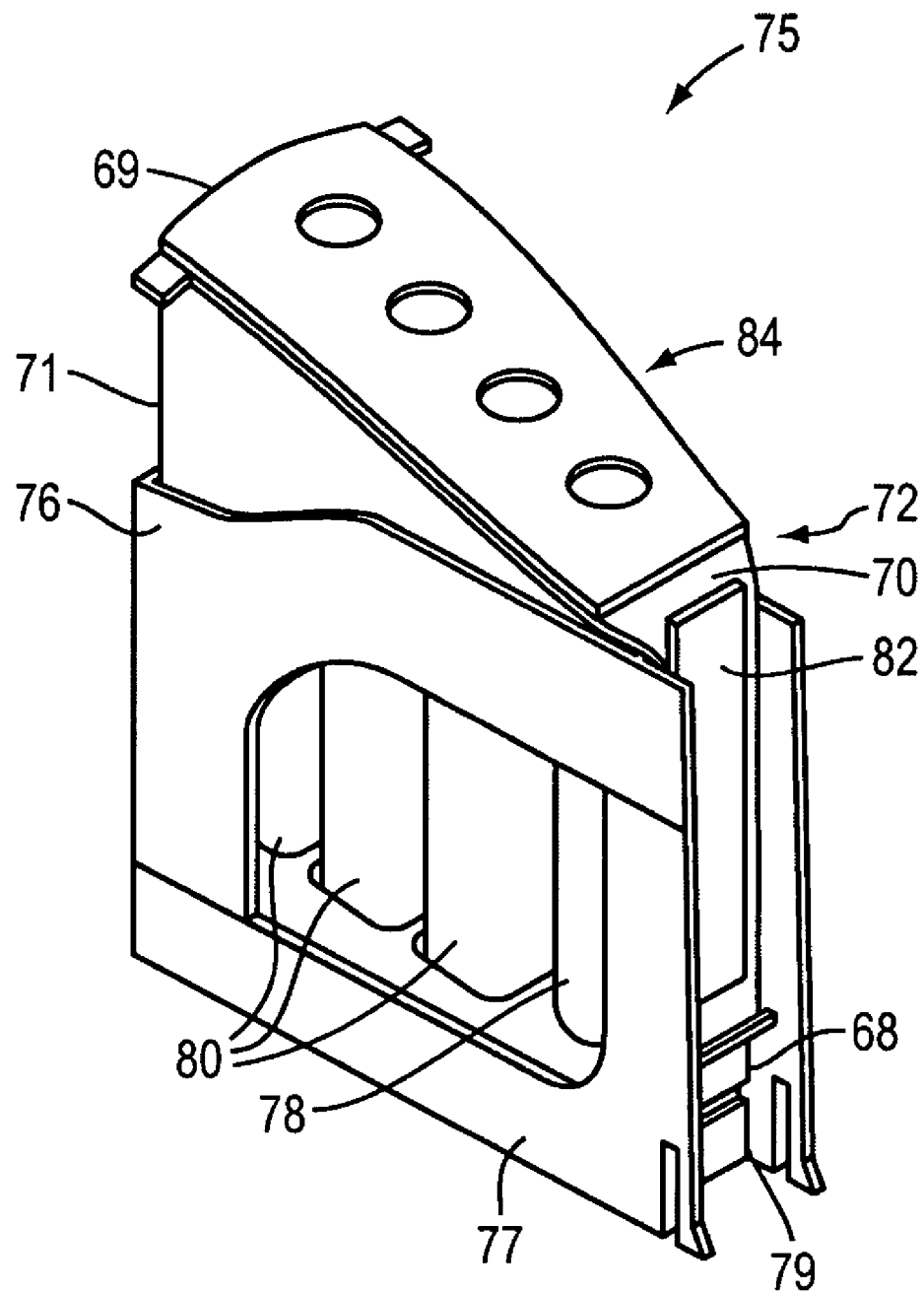
FIG. 2A is a perspective view of a reagent cartridge according to an exemplary embodiment of the present invention.

The reagent cartridge will now be described in more detail with reference to FIGS. 2A-2C. FIG. 2A is a perspective view of a reagent cartridge according to an embodiment of the present invention. The illustrated reagent cartridge 75 includes, for example, a channel 68, a holder 76, a base 77, a mixing tube 78, one or more reagent tubes 80, the bar code label 82, and a piercing cap assembly 84. The piercing cap assembly 84 includes a slide cap 69, a piercing cap 71, an access slide 72, including a spring 70, an evaporation cover 81 (not shown), and a leg 79. The piercing cap assembly 84 and its components will be discussed in more detail below. In some embodiments, the reagent cartridge 75 is a disposable package with one or more, preferably four, sealed tubes holding reagent or magnetic particles in a solution. Once the reagent cartridges 75 are placed within the reagent station 23 (not shown), the reagent cartridges 75 may be cooled, for example, to a temperature in the range of about, 4-8° C., more particularly at about six degrees Celsius. The chilling of the reagent cartridges 75 may improve the reagent shelf life.

Figure 2B:
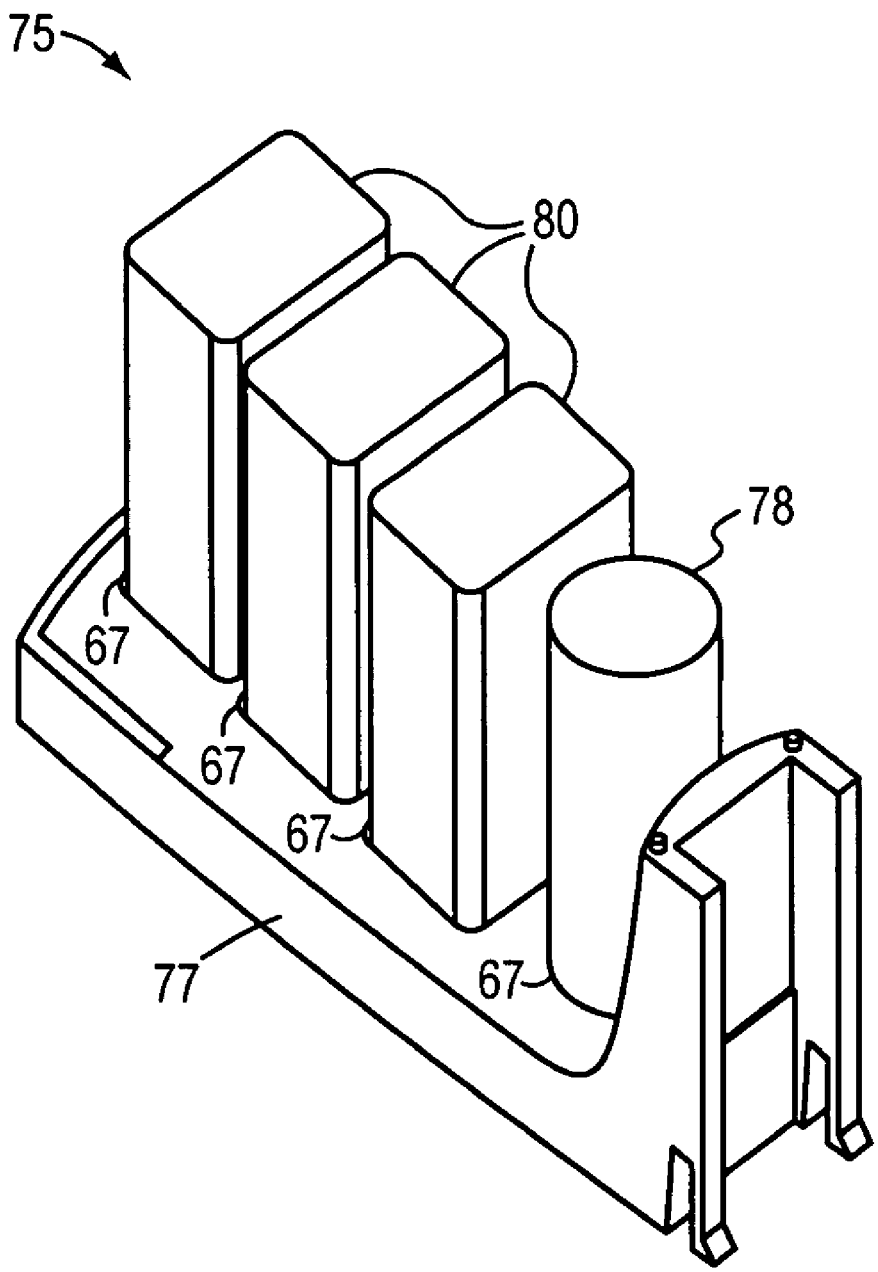
FIG. 2B is a perspective view of the reagent cartridge without a piercing cap assembly and holder according to an exemplary embodiment of the present invention.

FIG. 2B is a perspective view of the reagent cartridge 75 illustrating, the base 77, the mixing tube 78 and the reagent tubes 80, according to an embodiment of the invention.

With reference to FIG. 2B, the reagent tubes 80 are closed at the bottom end with an open, sealable top and contain the reagents necessary for performing certain clinical analyses. The cross-sectional shape through the short axis of the reagent tubes 80 may be of any shape to facilitate the storing of reagents, such as rectangular, square, circular, oval, or substantially circular. The reagent tubes 80 are sized to fit in the reagent cartridge 75 within the reagent station 23 (see FIG. 1). The reagent tubes 80 may be made of any relatively inert substance for storing reagents, for example, molded polypropylene, plastic, metal, or ceramic. The capacity of the reagent tubes 80 varies depending on their size but may range from about 1 milliliter to about 100 milliliters. Once appropriate reagents are introduced into the reagent tubes 80, in one embodiment, the top of the reagent tubes 80 are sealed, for example, with an aluminum polyester membrane. The reagent tubes 80 shown in FIG. 2B are sealed. The seal may be frangible. A plurality of protrusions 85 (see FIG. 2C) of the piercing cap assembly 84, described below, are positioned on the piercing cap assembly 84 to permit the user to break the seal when desirable.

With continued reference to FIG. 2B, the reagent tubes 80 and the mixing tube 78 are inserted into the base 77 either before or after the reagents are added into the tube. The base 77 may be molded plastic, e.g., ABS, sized to hold the required reagent tubes 80. In one embodiment, indentations or recesses 67, sized and shaped to engage the base of the reagent tubes 80 and the mixing tube 78 in the base 77, hold the reagent tubes 80 and the mixing tube 78 into the base 77. The reagent tubes 80 may be locked into the base 77. The lock may be, for example, a snap-lock. The reagent tubes 80 and the mixing tube 78 may also be detachable from the base 77.

Still referring to FIG. 2B, in one embodiment according to the invention, the mixing tube 78 contains the magnetic particle solution. The mixing tube 78 discussed in greater detail below, may be sized and made of material similar to the reagent tubes 80. Alternatively, other materials may be used to make the mixing tube 78. The magnetic particle solution is introduced into the mixing tube 78 either before or after the mixing tube is inserted into the base 77 of the reagent cartridge 75. Once a sufficient volume of magnetic particle solution in the mixing tube 78 is reached, the top of the mixing tube 78 may then be sealed. The mixing tube 78 shown in FIG.

2B is sealed. The seal may be frangible. The plurality of protrusions 85 (see FIG. 2C) of the piercing cap assembly 84, described below, may break the seal. In one embodiment, the seal is an aluminum polyester membrane.

The mixing tube 78 may be rotatably mounted, i.e., the mixing tube 78 may rotate while attached to the base 77, in an indentation or recess. In one embodiment, the mixing tube 78 is operably connected to a rotatable member operably joined to a motor. The rotatable member rotates the mixing tube 78 clockwise or counter-clockwise in order to suspend the magnetic particles in solution.

Figure 2C:
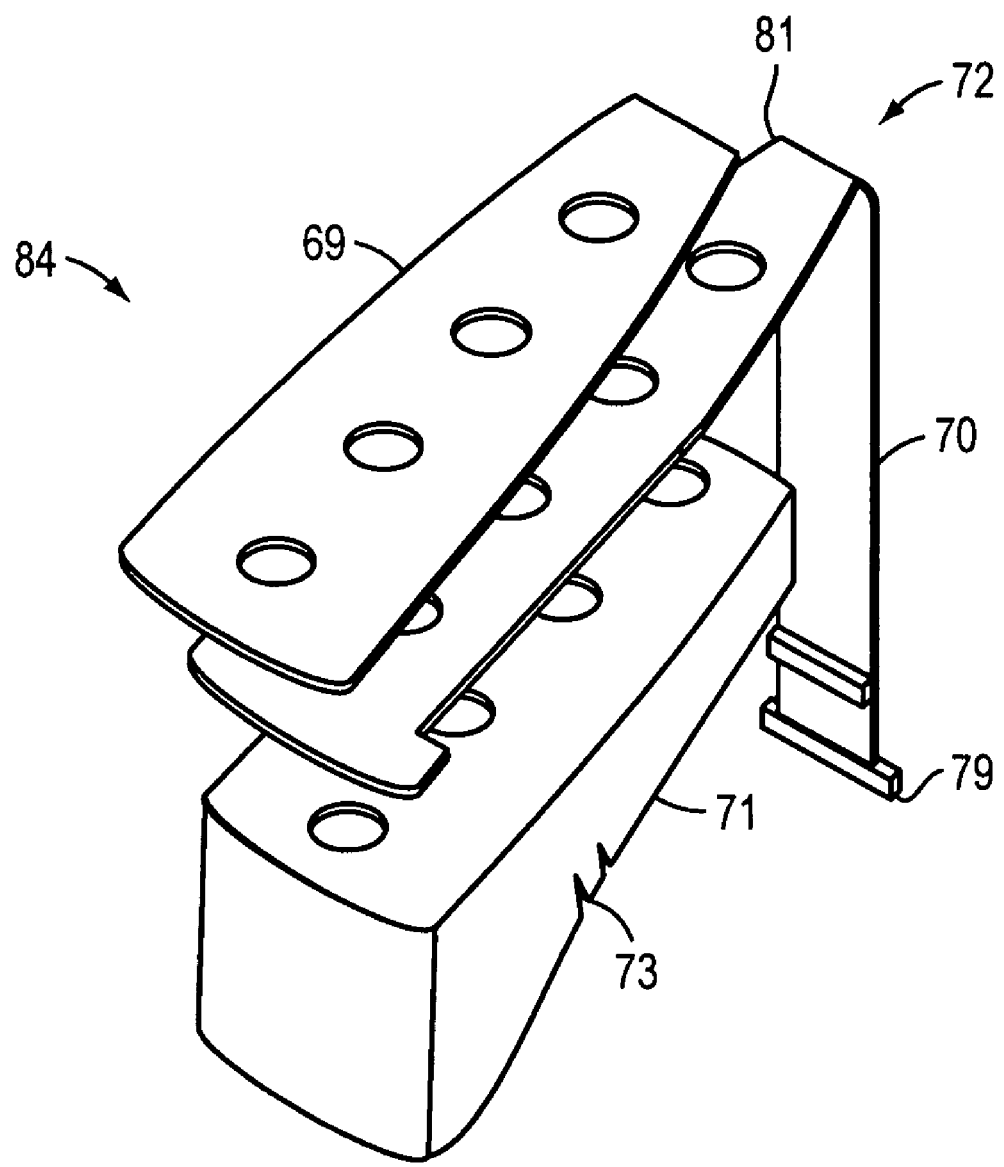
FIG. 2C is a perspective view of a piercing cap assembly according to an exemplary embodiment of the present invention.

FIG. 2C is a top perspective view of the piercing cap assembly 84. As noted above, the piercing cap assembly 84 includes the piercing cap 71, the slide cap 69, and the access slide 72, which includes the evaporation cover 81, the spring 70 and the leg 79. The access slide 72 is sandwiched between the piercing cap 71 and the slide cap 69. The slide cap 69 is a flat section of plastic with access holes to permit user to access the mixing tube 78 and reagent tubes 80. The slide cap 69 is sized to fit securely over the piercing cap 71 through, for example, ultrasonic welding or heat staking. Heat staking is a method of connecting separate components using plastic stud protruding from one component that fit into holes in a second component. The stud is then deformed through the softening of the plastic to form a head which mechanically locks the two components together.

The access slide 72, including the evaporation cover 81, the spring 70, and the leg 79 slides over the piercing cap 71 to permit access to the mixing tube 78 and reagent tubes 80 (not shown). The evaporation cover 81 is a flat rectangular section of plastic with access holes for permitting selective access to the mixing tube 78 and reagent tubes 80. When the evaporation cover 81 is in a first position with its holes aligned over the mixing tube 78 and reagent tubes 80 and the access holes of the slide cap 69, the evaporation cover 81 permits user access to the mixing tube 78 and reagent tubes 80. When it is in its second position, the access holes in the evaporation cover 81 are not aligned with the mixing tube 78 and the reagent tubes 80, thus sealing the mixing tube 78 and the reagent tubes 80 from the outside air and hindering evaporation of the solutions contained in the mixing tube 78 and the reagents in the reagent tubes 80.

Figure 2D:
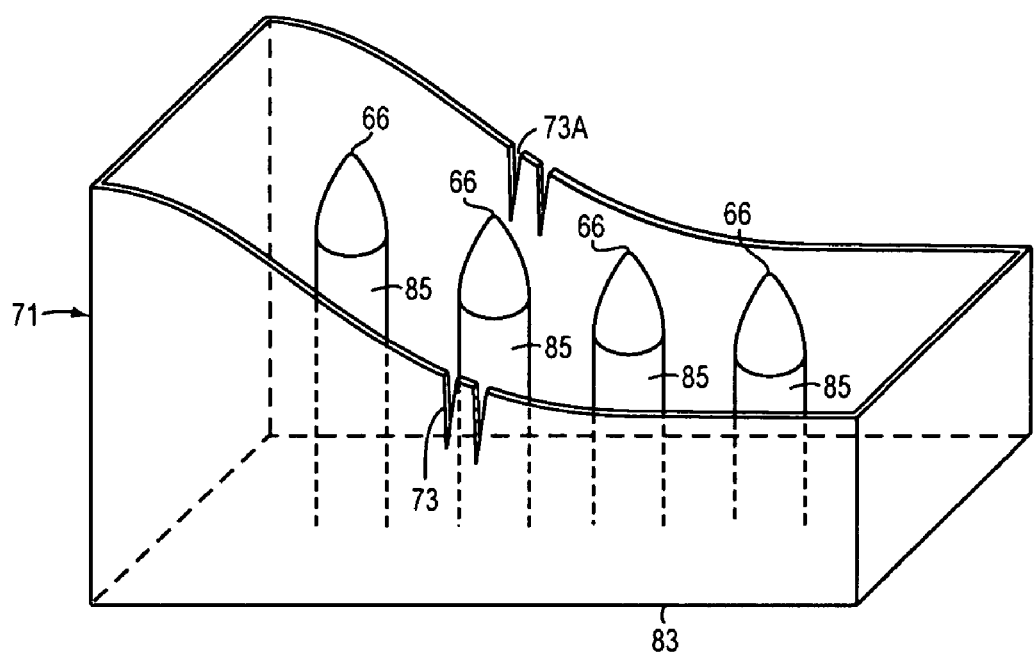
FIG. 2D is a perspective view of the piercing cap according to an exemplary embodiment of the present invention.

FIG. 2D is a perspective view of the bottom of the piercing cap 71. The piercing cap 71, a plastic cap sized to fit over the mixing tube 78 and reagent tubes 80, includes a lid 83, a first notch 73 and a second notch 73A, and one or more protrusions 85. The protrusions 85 may extend downward from the lid 83 of the piercing cap 71 into the reagent tubes 80 and mixing tube 78 (not shown). The protrusions 85 may be hollow cylinders with a beveled free end 66 to permit the puncturing of the frangible seal of the mixing tube 78 or reagent tube 80.

Figure 2E:
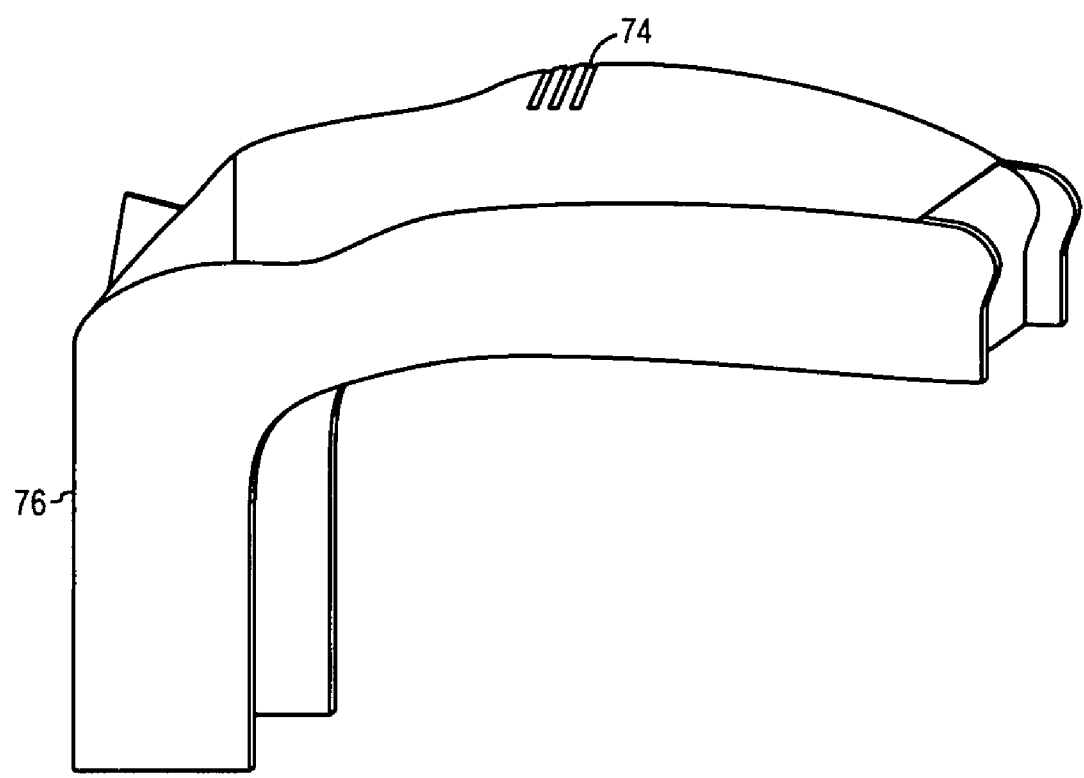
FIG. 2E is a perspective view of the reagent cartridge holder according to an exemplary embodiment of the present invention.

FIG. 2E is a perspective view of the holder 76. The holder 76, comprised of plastic, has a first groove 74 and a second groove (not shown) on the inside of the holder 76 for engagement with the piercing cap (not shown). The first groove 74 corresponds with first notch 73 (not shown) of the piercing cap and the second groove (not shown) corresponds to the second notch 73A (not shown) of the piercing cap. The interaction of the first notch 73 and the second notch 73A with the first groove 74 and the second groove will be discussed in more detail below.

With reference again to FIG. 2A, in typical operation, the piercing cap assembly 84 is positioned over the top of the reagent tubes 80 and the mixing tube 78. In one embodiment, the piercing cap assembly 84 is connected to the holder 76. The piercing cap assembly 84 may be mounted to the base 77 by hooking the leg 79 of the spring 70 into the channel 68 at the front of the base 77. The leg 79 may then slide in the channel 68, allowing the access slide 72 to move and permit access to the mixing tube 78 and reagent tubes 80. Alternatively, the piercing cap assembly 84 may be separable from the holder 76.

Referring to FIG. 2D, the protrusions 85 on the piercing cap assembly 84 may be hollow or the piercing cap assembly 84 may include one or more perforations to permit a pipette to pass through the protrusion 85 to aspirate reagents and magnetic particle solution from the reagent tubes 80 (not shown) and the mixing tube 78 (not shown) without requiring the removal of the piercing cap assembly 84. When depressed, for example, by a user, the protrusions 85 of the piercing cap assembly 84 puncture the seal on the reagent tubes 80 and the mixing tube 78. The piercing cap 71 remains depressed through the first notch 73 and the second notch 73A, located on the piercing cap 71, mating with the first groove 74 and the second groove (not shown) located in the holder 76 (shown in FIG. 2E). Once punctured, various pipettes may be inserted through one or more protrusions 85 to aspirate reagents from the reagent tubes 80 and magnetic particle solution from the mixing tube 78.

Figure 2F:
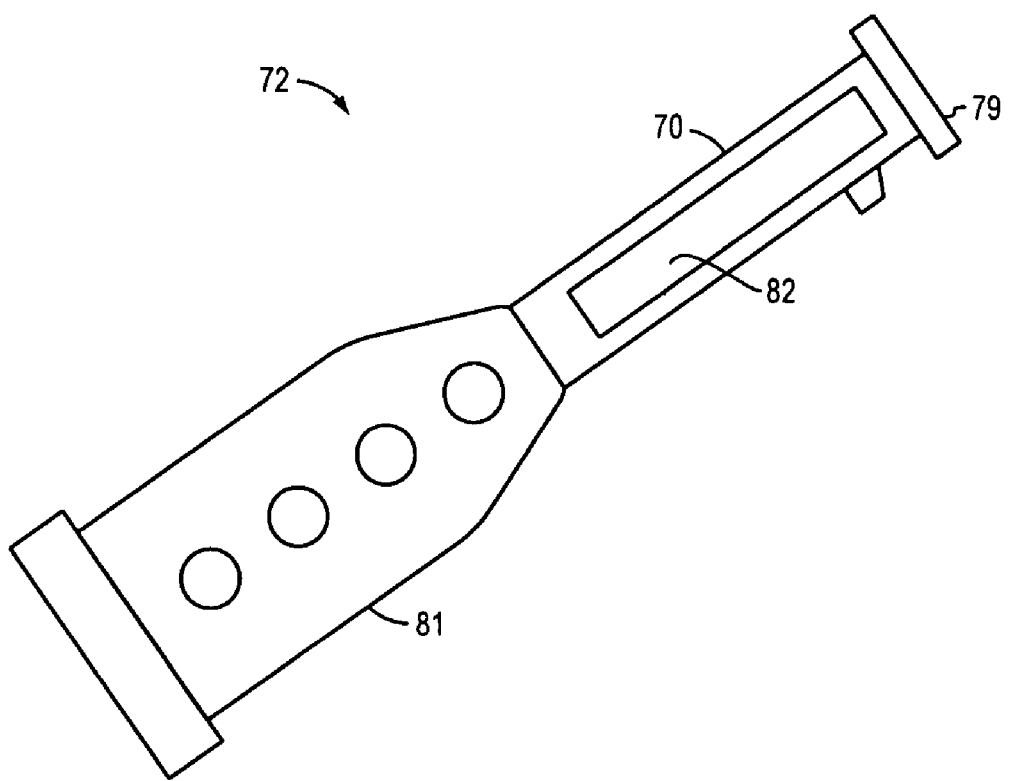
FIG. 2F is a perspective view of an access slide according to an exemplary embodiment of the present invention.

FIG. 2F is a perspective view of the access slide, comprised of plastic, of the piercing cap assembly. The spring 70 of the access slide 72 is, for example, a leaf spring that is biased to keep the reagent cartridge 75 closed when not in use. This access slide 72 is biased closed to minimize evaporation and contamination. Thus, once the reagent tubes 80 and mixing tube 78 have been punctured by the protrusions 85 of the piercing cap, evaporation of reagents and mixing tube solution can be prevented by sealing the reagent cartridge 75 with the evaporation cover 81 of the access slide 72.

As shown in FIG. 2A, to open the reagent cartridge 75 the spring 70 may be deflected by an attached stepper motor (not shown). Then, the leg 79 of the access slide 72 slides in the channel 68 of the base 77, thus sliding open the evaporation cover 81 (not shown) to allow user access to the reagent tubes 80 and mixing tube 78.

FIGS. 3A-3F depict a mixing tube 78 in more detail according to an embodiment of the present invention. Referring to FIGS. 3A-3F, in some embodiments, the mixing tube 78 is generally a cylinder including a wall 98, an interior surface 95, an opening at the top end 92, a lower section 96, an upper section 87, a floor 94, and a base 89. The upper section 87 extends from the top end 92 to the floor 94 of the mixing tube 78. The lower section 96 extends from the floor 94 to the base 89, which is on the opposite end of the tube 78 from the top end 92.

Figure 3A:
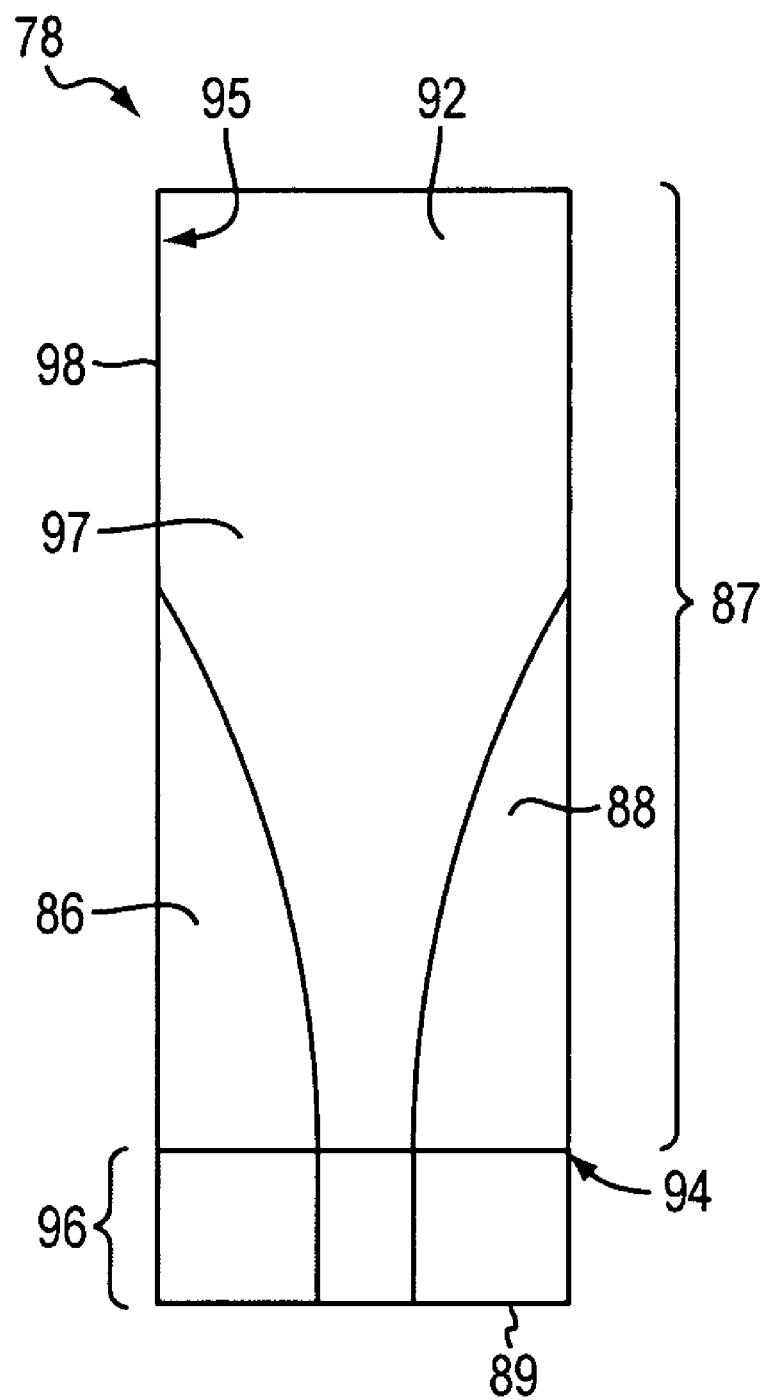
FIG. 3A illustrates a cross-section of the mixing tube illustrated in FIG. 3C taken at 3A-3A according to an exemplary embodiment of the present invention.
Figures 3B, 3C, 3D:
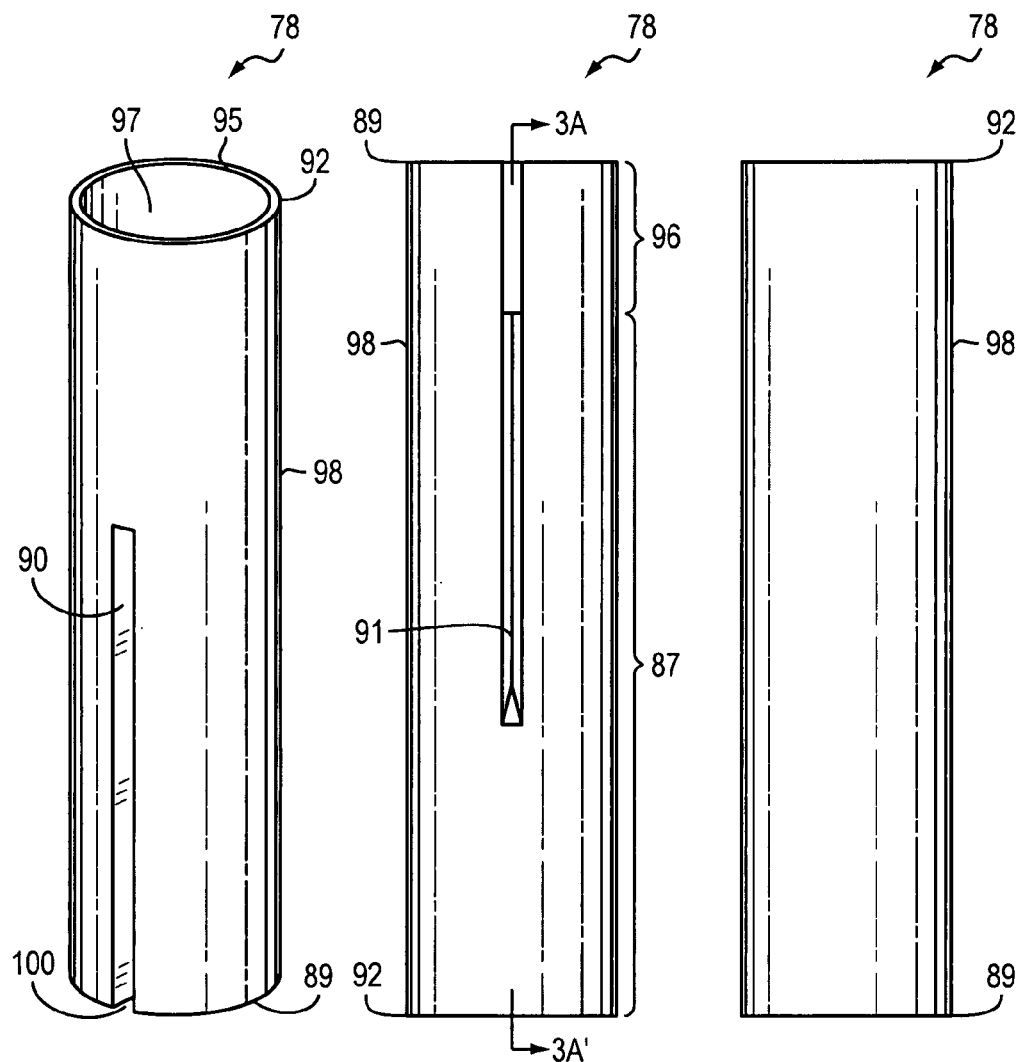
FIG. 3B is a side perspective view of the exterior surface according to an exemplary embodiment of the present invention.
FIG. 3C is another side perspective view of the mixing tube according to an exemplary embodiment of the present invention.
FIG. 3D is another side perspective view of the mixing tube according to an exemplary embodiment of the present invention.

With reference to FIG. 3A, a cross-section of the mixing tube through the plane 3A-3A' as shown in FIG. 3C, the tube floor 94 is the bottom most portion of the mixing tube 78 that holds the magnetic particle solution. The tube floor 94 may be, for example, flat, convex, or concave.

The lower section 96 of the mixing tube 78, as shown in FIGS. 3A, 3C, and 3E, is the section of the mixing tube 78 between the tube floor 94 and the base 89. With reference to FIG. 3E, the lower section 96 of the mixing tube 78 contains a longitudinally positioned cylindrical member 99, a first slot 100, a second slot 101, a first flange 102, and a second flange 103. The lower section 96 may extend approximately 5 to 25 millimeters beyond the tube floor 94. In one embodiment, a rotatable member may engage the lower section 96 to rotate the mixing tube 78.

With continued reference to FIGS. 3A-F, the wall 98 of the mixing tube 78 may be composed of molded polypropylene, plastic, ceramic, metal or any other inert material capable of storing a solution with magnetic particles. The capacity of the mixing tube 78 varies depending on their size but may range from about 1 milliliter to about 100 milliliters. The short-axis cross-sectional shape of the wall 98 may be circular. In one embodiment, the mixing tube 78 has a constant diameter or width from the opening 92 to the base 89 of the mixing tube 78. In a particular embodiment, the mixing tube is frustoconical, i.e., such that the opening 92 has a larger diameter than the base 89.

With reference to FIGS. 3A-F, the base 89 of the mixing tube 78 may be substantially flat to prevent unwanted oscillations of the mixing tube 78 during mixing and storage.

With reference to FIG. 3A, a cross-section of the mixing tube through the plane 3A-3A' as shown in FIG. 3C of an exemplary mixing tube 78 including a first agitating member 86 and second agitating member 88 is illustrated. The first agitating member 86 and the second agitating member 88 agitate the magnetic particles in solution in the mixing tube 78. The first agitating member 86 and the second agitating member 88 protrude into the lumen 97 of the mixing tube 78 and may extend from the mixing tube floor 94 to the mixing tube top end 92. Alternatively, the first agitating member 86 and the second agitating member 88 may extend from the mixing tube floor 94 to any point below the mixing tube top end 92.

With reference to FIG. 3A, the shape of the first agitating member 86 and the second agitating member 88 may be of any shape known to one of skill in the art that will create turbulence in the lumen 97 of the mixing tube 78 upon rotation of the mixing tube 78. For example, the cross-section of the first agitating member 86 and the second agitating member 88 may be triangular, circular, substantially circular, rectangular, square, or any other cross-sectional shape that will create turbulence in a solution held within the mixing tube 78. An exemplary first agitating member 86 and an exemplary second agitating member 88 may be flat or blade-like. Although only a first agitating member 86 and a second agitating member 88 are shown, multiple agitating members, such as three, four, five, or more, may be used and the invention is not limited to the illustrated embodiments.

In some embodiments, the first agitating member 86 and the second agitating member 88 may be formed by molding the inner surface 95 of the wall 98 of the mixing tube 78. As used herein formed by molding the inner surface 95 of the wall 98 means that the first agitating member 86 and the second agitating member 88 are not affixed to the tube 78, but are formed when the wall 98 of the mixing tube 78 is molded, for example, by extrusion molding.

When the mixing tube 78 is constructed via a molding process, the first agitating member 86 and the second agitating member 88 are formed by forcing the interior wall 95 of mixing tube 78 into the lumen 97 at certain sections of the outer wall. When viewed from the outside of mixing tube 78, the sections of the inner wall 95 that extend into the lumen 97 appear as grooves in the outer wall 98. A first groove 90 and a second groove 91 are depicted in FIGS. 3B, 3C, 3E and 3F. The first groove 90 and second groove 91 correspond to a first agitating member 86 and a second agitating member 88, as viewed from the lumen 97. Since no additional material is added to the mixing tube 78 to form the first agitating member 86 and the second agitating member 88, the wall 98 has a constant thickness along the length of the mixing tube 78, i.e. the wall 98 is not thicker where the first agitating member 86 and the second agitating member 88 are located. A constant thickness ensures even cooling and shaping during manufacturing.

Alternatively, the mixing tube 78 may be formed without the first groove 90 and the second groove 91 (not shown). In this embodiment, the first agitating member 86 and the second agitating member 88 are attached to the interior surface 95 of the wall 98 by an adhesive, thermal bonding, or a mechanical locking mechanism such as a snap-lock joint, for example.

With reference to FIGS. 3A, 3B, 3D, 3E, and 3F, in one embodiment, the first groove 90 and the second groove 91 originate at the base 89 of the mixing tube 78 as the first slot 100 and the second slot 101 in the lower portion 96 of the mixing tube 78 as shown in FIGS. 3E and 3F, respectively, and extend along the length of the mixing tube 78 to or nearly to the top end 92. In one embodiment, the first groove 90 and the second groove 91 extend approximately two thirds of the length of the mixing tube 78 from the base 89 toward the top end 92 of the mixing tube 78.

FIG. 4 is a top-view of the mixing tube according to an embodiment of the present invention. This view shows the first agitating member 86 and the second agitating member 88 protruding into the lumen 97 of the mixing tube.

FIG. 5 is a bottom-view of the mixing tube according to an embodiment of the present invention. The wall 98 of the lower section 96, may not be one continuous section. Rather, in one embodiment, the wall 98 has one or more slots, for example, the first slot 100 and the second slot 101, which may eventually form the first groove 90 and second groove 91 (shown in FIGS. 3E and 3F). FIG. 5 also depicts the longitudinally positioned cylindrical member 99, the first flange 102, and the second flange 103. The longitudinally positioned cylindrical member 99, the first flange 102, and the second flange 103 may assist in the engagement of the mixing tube 78 by a motor. The rotation of the mixing tube 78 via an attached motor will be discussed in more detail below.

In another aspect, the invention is directed to a method of uniformly suspending the magnetic particles in a solution in a mixing tube 78 according to the invention described above. According to one embodiment of the method of the invention, before a sample probe aspirates magnetic particle solution from the mixing tube 78 into a sample vial, the magnetic particles are suspended in the mixing tube 78. The magnetic particles are suspended by the first agitating member 86 and the second agitating member 88 rotating or oscillating to create turbulence in the solution. The turbulence agitates the magnetic particles and suspends them in solution.

Figure 6:
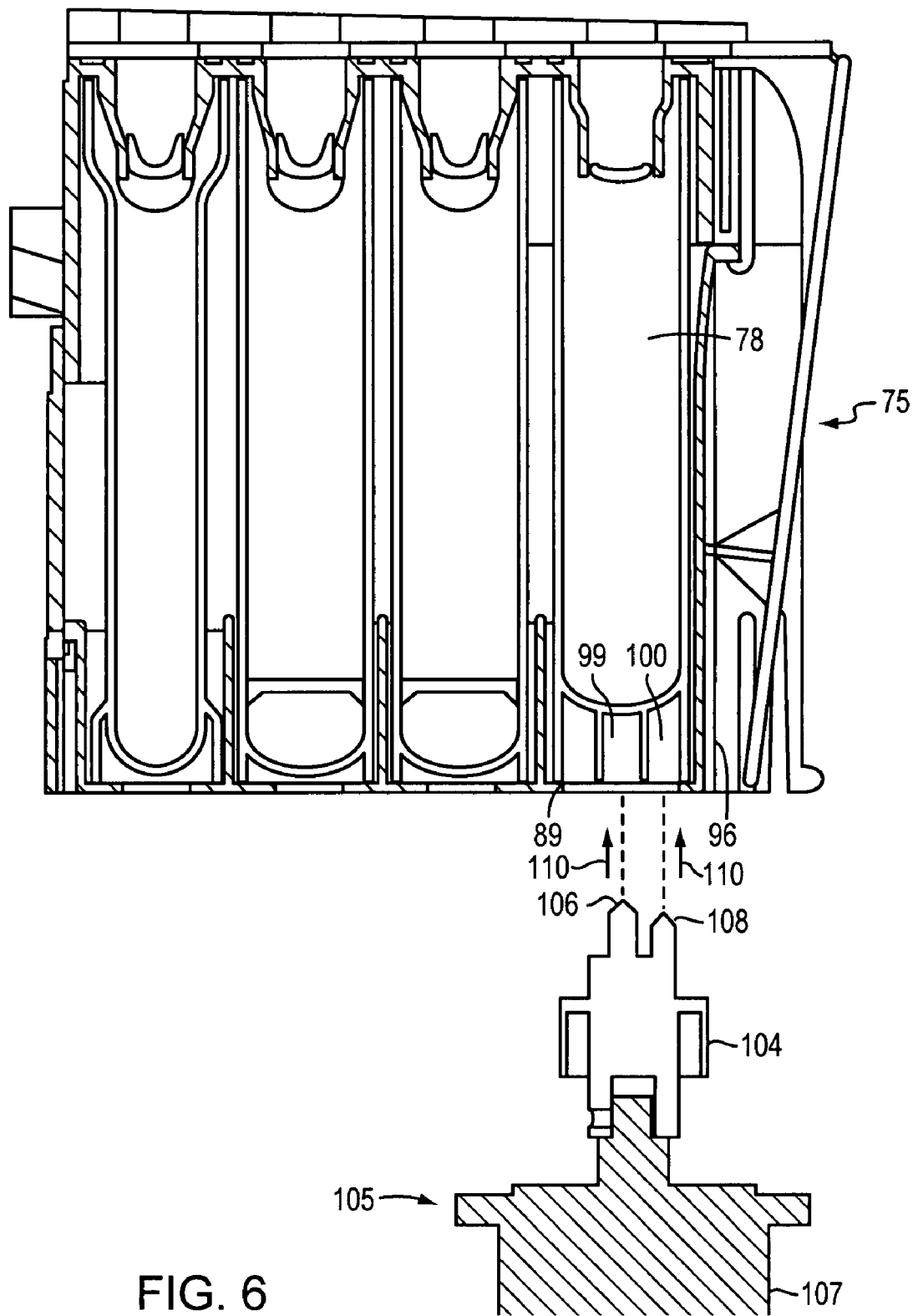
FIG. 6 is a perspective view of a motor and the reagent cartridge according to an exemplary embodiment of the present invention.

As shown in FIG. 6, in order to rotate or oscillate the mixing tube 78 to create the turbulence, a motor 105 may be used. The motor 105 may combine a stepper motor 107 for rotation and a linear actuator 104 for movement in the Z-direction, shown by the dotted lines in FIG. 6, relative to the motor. The linear actuator 104 may be capable of, for example, in the range of 10 to 25 mm of travel, such as 10 mm, 15, mm, 20 mm or 25 mm, in the Z-direction. In a particular embodiment, the stepper motor 107 may rotate bi-directionally.

In operation, the linear actuator 104 is first raised to engage the mixing tube 78. Then, the stepper motor 107 rotates the mixing tube according to a mixing protocol, i.e. a series of rotations used to suspend the magnetic particles, and then the rotatable member is lowered to disengage from the mixing tube 78.

With reference to FIG. 6, according to one embodiment of the invention, the linear actuator 104 has one or more pins, for example, a first pin 106 and a second pin 108. The second pin 108 may engage the first slot 100 of the mixing tube 78 as indicated by arrows 110. The first pin 106 may engage the cylindrical member 99 located at the lower section 96 of the mixing tube 78.

In another embodiment (not shown), the lower section 96 of the mixing tube 98 may include a plurality of longitudinally placed cylindrical members 99. Additional pins (not shown) may then engage each separate cylindrical member to rotate the mixing tube clockwise and counter-clockwise in an oscillating manner. In yet another embodiment (not shown), a gear may be affixed to the base 89 of the mixing tube 78. The rotatable member may then engage the gear to rotate the mixing tube 78 both clockwise and counter-clockwise.

According to one embodiment of the method of the invention, the mixing tube 78 rotates in one or more directions to agitate the magnetic particles. In a particular embodiment, the mixing tube 78 is first rotated in one direction, for example clockwise, for a first time period and then rotated in the opposite direction, for example counter-clockwise, for a second time period. In another embodiment, the mixing may involve separate phases, such as two phases, three phases, four phases or more. Each phase may be composed of one rotation in one direction of a predetermined number of complete or partial rotations, followed by one rotation a predetermined number of complete or partial rotations in another direction. The series of rotations is repeated several times. Thus, the variables associated with the mixing process include (1) rotation direction, (2) amplitude of rotation or degrees/angle of rotation and (3) number of rotations. The first phase and the second phases rotate the mixing tube 78 through different angles and the mixing tube 78 is rotated a different number of times for each phase.

For example, in an exemplary mixing protocol, the first phase, may include one full rotation in each direction and alternating the direction of rotation fifteen times thereafter. The first phase of mixing may last up to about 6.8 seconds and may involve an oscillation time of about 0.452 seconds. The second phase, may involve four full rotations in each direction and alternating the direction of rotation three times. The second phase mixing may be up to about 3.0 seconds and the oscillation time may be about 1.01 seconds. The total mixing time of both phases may be about 10.6 seconds, including raising and lowering the rotatable member and mixing in both the first phase and the second phase. Depending on the level of mixing required, the mixing protocol may repeat two, three or more times to obtain the desired suspension of magnetic particles. Furthermore, the above described sequence may be repeated two times per instrument cycle to accomplish the desired amount of magnetic particle re-suspension. The process and method of mixing and suspending the magnetic particles is not limited to the examples disclosed herein, but can be accomplished through any mixing protocol that would ensure uniform suspension of the magnetic particle solution.

Another aspect of the present teachings relates to a method of manufacturing the mixing tube 78. The mixing tube may be manufactured by molding, for example, extrusion molding or injection molding. Injection molding, as known by one of skill in the art, involves injecting molten material into a mold to form the desired shape. Extrusion molding, as known by one of skill in the art, involves the forcing of molten material through a dye to form the desired shape. In an extrusion molding method of manufacturing, manufacturing the mixing tube 78 in a frustoconical shape is advantageous because it facilitates the removal of the mixing tube 78 from a die in which it was molded.

Variations, modification, and other implementations of what is described herein will occur to those of ordinary skill in the art without departing from the spirit and scope of the invention as claimed. Accordingly, the invention is to be defined not by the preceding illustrative description but instead by the spirit and scope of the following claims.

What is claimed is:

1. A system for suspending particles, said system comprising:
   a reagent cartridge comprising a reagent holder for holding a plurality of tubes;
   a plurality of tubes comprising:
   a mixing tube for holding particles, said mixing tube having a volumetric capacity in the range of about 1 milliliter to about 100 milliliters, rotatably mounted in said holder, said mixing tube comprising a top end and a lower section positioned on an end opposite to said top end, an interior surface, an exterior surface, a first agitating member, and a second agitating member, each of said first agitating member and said second agitating member formed by extending said interior surface of the mixing tube into the lumen of said mixing tube, the dimensions and positioning of said first agitating member aligned with a first longitudinal groove on said exterior surface of said mixing tube and the dimensions and positioning of said second agitating member aligned with a second longitudinal groove on said exterior of said mixing tube, said mixing tube further comprising at least one slot and a cylindrical member, longitudinally positioned on said lower section of said mixing tube;
   said reagent holder comprising a body including a first groove and a second groove;
   a piercing cap assembly positioned over the plurality of tubes, the piercing cap assembly comprising a piercing cap including a first notch, a second notch and one or more protrusions extending from the piercing cap, each protrusion comprising a hollow cylinder, wherein said first notch of said piercing cap engages with said first groove of said reagent holder and said second notch of said piercing cap engages with said second groove of said reagent holder when said piercing cap is in a depressed position; and
   a plurality of magnetic particles positioned in the lumen of said mixing tube.

2. The system of claim 1 further comprising a motor operatively connectable to said slot and said cylindrical member, said motor having a linear actuator for engaging said slot and said cylindrical member via two pins, wherein rotation of said cylindrical member actuates said agitating members thereby suspending said particles.

3. The system of claim 1, wherein said first agitating member is opposite said second agitating member.

4. The system of claim 1 further comprising a third agitating member.

5. The system of claim 1, wherein said first agitating member and said second agitating member are substantially triangular in cross-section.

6. The system of claim 1, wherein said first agitating member and said second agitating member are substantially semicircular in cross-section.

7. The system of claim 1, wherein said first agitating member and said second agitating member are substantially rectangular in cross-section.

8. The system of claim 1, wherein said first agitating member and said second agitating member are blades.

9. The system of claim 2 wherein said linear actuator further comprises a third pin and said mixing tube further comprises a second slot for engaging with said third pin of said linear actuator.

10. The system of claim 1, wherein said mixing tube is cylindrical.

11. The system of claim 1 wherein said mixing tube is frustoconical.

12. The system of claim 1 wherein said mixing tube is sealed.

13. The system of claim 1, wherein said mixing tube is extrusion molded.

14. The system of claim 1, wherein said mixing tube is detachable from said holder.

15. The system of claim 1 further comprising a plurality of reagent tubes.

16. The system of claim 15 wherein each of said plurality of reagent tubes is detachable from said holder.

17. The system of claim 15 wherein at least one of said plurality of reagent tubes is substantially rectangular in cross-section.

18. The system of claim 15 wherein at least one of said plurality of reagent tubes is substantially cylindrical.

19. The system of claim 1 wherein said mixing tube comprises a wall of uniform thickness.

* * * * *

UNITED STATES PATENT AND TRADEMARK OFFICE
CERTIFICATE OF CORRECTION

| | |
|---|---|
| PATENT NO. | : 7,731,414 B2 |
| APPLICATION NO. | : 11/704001 |
| DATED | : June 8, 2010 |
| INVENTOR(S) | : Vincent et al. |

It is certified that error appears in the above-identified patent and that said Letters Patent is hereby corrected as shown below:

On the title page, item (73) Assignee "Instrumentation Laboratory Company, Bedford, MA (US)" should read -- Biokit, S.A., Barcelona (ES) --

Signed and Sealed this
Nineteenth Day of April, 2011

David J. Kappos
*Director of the United States Patent and Trademark Office*